United States Patent [19]

McCain, Jr.

[11] 4,304,732

[45] Dec. 8, 1981

[54] ALKYLENE OXIDE-SULFUR DIOXIDE COPOLYMER SURFACE ACTIVE AGENTS

[75] Inventor: James H. McCain, Jr., Charleston, W. Va.

[73] Assignee: Union Carbide Corporation, New York, N.Y.

[21] Appl. No.: 107,016

[22] Filed: Dec. 26, 1979

[51] Int. Cl.$^3$ .......................................... C07C 137/00
[52] U.S. Cl. .............................. 260/456 NS; 252/549
[58] Field of Search ................................. 260/456 NS

[56] References Cited

U.S. PATENT DOCUMENTS 2,497,135  2/1950  Myles et al. .................. 260/456 NS
3,179,687  4/1965  Covey et al. ................. 260/456 NS

*Primary Examiner*—Nicky Chan
*Attorney, Agent, or Firm*—Franklyn Schoenberg

[57] ABSTRACT

A nonionic composition that exhibits activity as a surface active agent is provided which comprises the alkylene oxide-sulfur dioxide copolymer adducts of a water soluble alcohol.

4 Claims, No Drawings

ALKYLENE OXIDE-SULFUR DIOXIDE COPOLYMER SURFACE ACTIVE AGENTS

The present invention relates to a new class of nonionic surface active agents that are alkylene oxide and sulfur dioxide copolymer adducts of water soluble alcohols having at least two carbon atoms and to the process of preparing the same.

Nonionic surface active agents including, for example, polyoxyalkylated alkylphenols, polyoxyalkylated fatty alcohols, polyoxyalkylated fatty acids, polyoxyalkylated fatty mercaptans, polyoxyalkylated fatty amines, polyoxyalkylated fatty amides, and polyoxyalkylated water-insoluble polyols are well known commercial products as is their method of preparation. The usual structure of these materials is $R(OE)_n$, where R represents the residue of an alcohol, polyol, amine, carboxylic acid or phenol, R is a hydrophobic group, OE is poly(alkylene oxide), and n is usually one or two.

Although the wide range of products that are known may be employed in many different applications, it is certainly desirable to develop new compositions which are surface active agents and may offer some economic or other advantages.

SUMMARY OF THE INVENTION

In accordance with the present invention there is provided a novel class nonionic compositions that exhibit activity as surface active agents which comprise the alkylene oxide-sulfur dioxide copolymer adducts of water soluble alcohols having at least two carbon atoms. In general the compositions of the present invention may be represented by the following general formulae I and II.

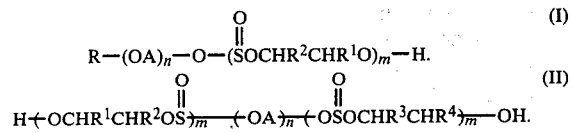

wherein R is an alkyl group, $R^{1, 2, 3, 4}$ can be the same or different and is hydrogen or an alkyl group, n is any integer up to a value of about 1000, and preferably in the range of 5 to about 500 and m is any integer up to a value of about 1000. OA is a divalent radical selected from the group consisting of oxyethylene units and mixtures of oxyethylene units and oxypropylene units having oxypropylene units up to a ratio of about 1:1.

The compositions of the invention are surface active agents that will reduce the surface tension characteristics of water. Moreover, depending on the value of n and m, the cloud point of the compositions in water can be varied from about 0° C. to about 100° C.

DESCRIPTION OF THE INVENTION

The compositions of the invention correspond to the general formulae I and II below.

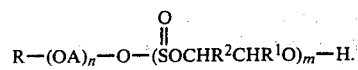

wherein R is an alkyl group having from 1 to about 20 carbon atoms, OA is a divalent radical selected from the group consisting of oxyethylene units and mixtures of oxyethylene units and oxypropylene units having oxypropylene units up to a ratio of about 1:1, n is an integer having a value up to about 1000 and preferably is an integer having values of 5 to about 500. $R^1$ and $R^2$ may be the same or different and is hydrogen or an alkyl group having 1 or 2 carbon atoms, and m is an integer having a value up to about 1000, and preferably having values from 3 to 500. In the compositions of this invention the portion of the chain $R—(OA)_n$ is the hydrophile or water soluble portion of the molecule, and the

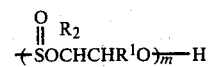

portion of the chain is the hydrophobe or water insoluble portion of the molecule.

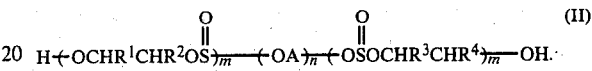

wherein $R^{1, 2, 3, 4}$ may be the same or different and is hydrogen or an alkyl group having 1 or 2 carbon atoms and m is an integer having a value up to about 1000, and preferably having values from 3 to 500. OA is a divalent radical selected from the group consisting of oxyethylene units and mixtures of oxyethylene units and oxypropylene units having oxypropylene units up to a ratio of about 1:1, and n is an integer having a value up to about 1000 and preferably values of 5 to about 500.

In the compositions of the invention having the general formula II, the portion of the chain $—(OA)_n$ is the hydrophile or water soluble portion of the molecule, and the

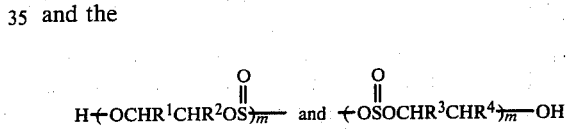

portions of the chain are the hydrophobe or water insoluble portion of the molecule.

The compositions of the invention having the general formula I, above, are, in general, prepared by reacting a mixture of an alkylene oxide and sulfur dioxide with a water soluble alcohol having at least 3 carbon atoms and only one reactive hydrogen in the presence of a basic catalyst.

The reaction may be conducted in a conventional manner, that is, the reactive hydrogen compound and the catalyst are placed in a reactor, alkylene oxide and sulfur dioxide are added at the reaction temperature until the desired number of moles have been reacted, and the product is removed from the reactor and neutralized. The sulfur dioxide should be added in an amount at least equivalent to or in excess of the number of moles of alkylene oxide that is added. The reaction may be conducted in the presence of a solvent, but usually a solvent is not employed.

The temperature at which the reaction proceeds is not narrowly critical and generally products can be made at a reasonable rate of reaction and without decomposition of the reactants or reaction products at a temperature between about 0° C. to 150° C. with a temperature between about 30° C. and 100° C. being generally preferred. While the pressure of the reaction is not narrowly critical, when low-boiling alkalene oxides, such as ethylene oxide and propylene oxide are employed, a pressurized reactor is preferably used.

Alcohols that are suitable for use in preparing compositions of the invention characterized by formula I are water soluble primary and secondary aliphatic alcohols which are straight or branched chain having at least three carbon atoms, only one reactive hydrogen or hydroxyl group, and from one oxyethylene unit to about 1000, and preferably to about 100, oxyethylene units or mixture of oxyethylene and higher oxyalkylene units in a ratio up to about 1:1 of higher oxyalkylene units. Exemplary of such suitable alcohols are glycol ethers such as ethylene glycol monomethyl ether, ethylene glycol monoethyl ether, ethylene glycol monobutyl ether, diethylene glycol monomethyl ether, and diethylene glycol monoethyl ether; methoxytriethylene glycol and methoxypolyethylene glycols having a molecular weight from about 200 to about 20,000 such as are commercially available under the trademark designation CARBOWAX Methoxy Polyethylene Glycols from Union Carbide Corporation; and polyalkylene glycols such as butoxy polyalkylene glycols available commercially under the trademark designation UCON fluids Series 50HB from Union Carbide Corporation.

The composition of the invention characterized by formula II, above, can be prepared by reacting an alkylene oxide and sulfur dioxide with a water soluble alcohol having at least 2 carbon atoms and only two reactive hydrogens in the presence of a basic catalyst.

The reaction may be conducted in a conventional manner as hereinabove described with the sulfur dioxide being used in an amount at least equivalent to, or in excess of, the number of moles of alkylene oxide that is added.

Alcohols suitable for use in preparing compositions of the invention characterized by general formula II are water soluble, primary and secondary aliphatic diols which are straight or branched chain having at least two carbon atoms and from one oxyethylene unit to about 1000, and preferably to about 100 oxyethylene units or mixtures of oxyethylene and higher oxyalkylene units. Exemplary of such suitable diols are ethylene glycol, diethyl glycol, triethylene glycol, polyethylene glycols having a molecular weight from about 200 to about 20,000 such as are commercially available under the trademark designation CARBOWAX Polyethylene Glycols from Union Carbide Corporation, and polyalkylene glycols prepared from a mixture of ethylene oxide and propylene oxide available commercially under the trademark designation UCON fluids, series 75H from Union Carbide Corporation.

It may be mentioned that compositions generally characterized by formula II where the number of hydrophobe groups is the same as the number of hydroxyl groups in the starting alcohol may also be prepared from water soluble, aliphatic polyols having more than two hydroxyl groups up to as many as six such hydroxyl groups, at least 3 carbon atoms and from three oxyethylene units to about 1000, and preferably, to about 100 oxyethylene units or mixture of oxyethylene and higher oxyalkylene units. Exemplary of such polyols may be water soluble alkylene oxide adducts of trihydric alcohols such as glycerine and trimethylolpropane; tetrahydric alcohols such as pentaerythritol; and hexahydric alcohols such as sorbitol and mannitol.

Alkylene oxides suitable for use in preparing compositions of the invention in combination with sulfur dioxide have from 2 to 4 carbon atoms and include, for example, ethylene oxide, 1,2-propylene oxide, 1,2-butylene oxide, and mixtures thereof.

The number of moles of alkylene oxide and sulfur dioxide employed in preparing compositions of the present invention may vary widely depending on the reactive hydrogen compound to be adducted and the particular application for which the composition is to be employed. It is important, however, that the number of moles of sulfur dioxide added are in an amount at least equivalent to the number of moles of alkylene oxide that are added.

In preparing the compositions of the invention, the reaction of the reactive hydrogen compound and mixtures of alkylene oxide and sulfur dioxide is catalyzed by the presence of a basic catalyst. It has been found that not only is a weakly basic material such as quinoline suitable as a catalyst for the reaction but that strongly basic materials such as potassium hyroxide and sodium hydroxide are even more effective catalysts for the reaction and are, accordingly, preferred. The amount of catalyst to be used is not narrowly critical and a catalytic effect has been noted with only a small amount thereof being present.

The invention will become more clear when considered together with the following examples which are set forth as being merely illustrative of the invention and which are not intended, in any manner, to be limitative thereof. Unless otherwise indicated, all parts and percentages are by weight.

EXAMPLE 1

A 1-liter rocking autoclave cooled with liquid nitrogen was charged with 150 grams (0.2 moles) of methoxypolyethylene glycol available commercially under the trademark designation CARBOWAX Methoxy Polyethylene Glycol 750 from Union Carbide Corporation, having a molecular weight of 750, 88 grams (2.0 moles) of ethylene oxide, 140 grams (2.2 moles) of sulfur dioxide, and 4.0 grams (0.03 moles) of the catalyst quinoline. The autoclave was sealed and heated at 60° C. for 18 hours. A liquid product was recovered from the autoclave, and after vacuum stripping to remove excess sulfur dioxide, was determined to weigh 352 grams.

The liquid product was analyzed and was determined by the Gel Permeation Chromatography technique to have a molecular weight of 1400; and by Infra red adsorption and Nuclear magnetic resonance adsorption procedures as having the structure respresented by formula I wherein R was methyl, n was about 16, $R^1=R^2$ and was hydrogen, and m was equal to about 6.

The product was also determined to have a cloud point (1% aqueous solution; ASTMD-2024) of 54.5° C., and reduced the surface tension of water from 72.1 to 55.3 dynes/cm (0.1% aqueous solution).

EXAMPLE 2

A 100 cc stainless steel rocking autoclave was charged with 25 grams (0.025 moles) of polyethylene glycol having a molecular weight of 1000, available commercially under the trademark designation CARBOWAX Polyethylene Glycol 1000, and 1.0 (0.008 moles) of quinoline. The autoclave was cooled in liquid nitrogen and 11 grams (0.25 moles) of ethylene oxide and 19 grams (0.30 moles) of sulfur dioxide were added thereto. The autoclave was sealed and heated at 60° C. for 18 hours. A liquid product was recovered from the autoclave and, after vacuum stripping to remove excess sulfur dioxide, was found to weigh 51.5 grams.

The molecular weight of the product as determined by gel permeation chromatography was indicated to be 1790, and analytical data obtain by nuclear magnetic resonance absortion identified the product as having the structure of formula II wherein n was about 23, $R^1=R^2=R^3=R^4=$ hydrogen, and m was about 4. The product was also determined to have a cloud point in water (1% solution) of 38° C.

EXAMPLE 3

Using the apparatus and procedure of Example 2, 18.8 grams (0.0047 moles) of polyethylene glycol having a molecular weight of 4000, available commercially under the trademark designation CARBOWAX 4000 from Union Carbide Corporation, 14.5 grams (0.26 moles) of propylene oxide, 19 grams (0.30 moles) of sulfur dioxide, and 1.0 gram (0.008 moles) of quinoline were reacted.

A liquid product weighing 45.7 gram was obtained which by gel permeation chromatography had a molecular weight of 5140 and was identified by NMR to have the structure of formula II wherein n was about 91, $R^1=R^3=CH$, $R^2=R^4=$ hydrogen, and m was about 5. The product had a cloud point in water (1% solution) of 72° C., and at 21° C. reduced the surface tension of water (0.1% solution) from 72.6 to 47.3 dynes/cm.

EXAMPLE 4

A series of experimental reactions were run with two types and different amounts thereof of monohydroxyl alchols and with different mixtures of alkylene oxides. The proportions and types of ingredients used in each of the reactions is summarized in Table 1.

TABLE I

| | | | | | | |
|---|---|---|---|---|---|---|
| PEG A (moles) | 0.02 | 0.025 | 0.033 | — | — | — |
| PEG B (moles) | — | — | — | 0.007 | 0.010 | 0.013 |
| ethylene oxide (moles) | 0.25 | 0.125 | — | 0.25 | 0.125 | — |
| propylene oxide (moles) | — | 0.125 | 0.25 | — | 0.125 | 0.25 |
| sulfur dioxide (moles) | 0.3 | 0.3 | 0.3 | 0.3 | 0.3 | 0.3 |
| potassium hydroxide | 0.8* | 0.8* | 0.8* | 0.8* | 0.8* | 0.8* |

*quantity used was in millimoles

The alcohol employed in reactions A, B, and C was methoxypolyethylene glycol having a molecular of 750 and in reactions D, E, & F was methoxypolyethylene glycol having a molecular weight of 2000.

In each of the experimental reactions of this example the following procedure was used:

To a weighed quantity of the alcohol was added to the potassium hydroxide catalyst and the mixture was heated at 110° C. and 5 mm pressure. The mixture was transferred to a 100 cc stainless steel rocking autoclave and the autoclave was cooled in liquid nitrogen. A mixture of the alkylene oxide and sulfur dioxide was then added to the autoclave which was sealed. The sealed autoclave was heated at 60° C. for approximately 18 hours. The autoclave was then cooled, the product was discharged and heated at 60° C. and 5 mm pressure to remove excess sulfur dioxide.

The molecular structures of the products are summarized in Table II along with cloud point properties. All of the products produced were determined to have a structure corresponding to formula I.

TABLE II

| Experimental Reaction | R | n | $R^1$ | $R^2$ | m | Cloud Point, °C. |
|---|---|---|---|---|---|---|
| A | CH$_3$ | 16 | H | H | 13 | 29 |

TABLE II-continued

| Experimental Reaction | R | n | $R^1$ | $R^2$ | m | Cloud Point, °C. |
|---|---|---|---|---|---|---|
| B | CH$_3$ | 16 | 50% H 50% CH$_3$ | H | 10 | 45 |
| C | CH$_3$ | 16 | CH$_3$ | H | 8 | 51 |
| D | CH$_3$ | 45 | H | H | 20 | 92 |
| E | CH$_3$ | 45 | 50% H 50% CH$_3$ | H | 26 | 88 |
| F | CH$_3$ | 45 | CH$_3$ | H | 36 | 91 |

Each of the compositions prepared in this Example were evaluated for soil release and soil removal properties, and surface tension properties using standard known, test procedures and compared with a commercial surface active agent which was an ethylene oxide adduct (7 moles average) of mixed linear primary alcohols having from 12 to 15 carbon atoms. A summary of the results obtained are reported in Table III.

TABLE III

| Sample | Soil Release[a] (% Soil removal) | Soil Removed[b] (% detergency) | Surface Tension[c] (dynes/cm) |
|---|---|---|---|
| A | 46 | 1 | 46 |
| B | 53 | 0 | 50 |
| C | 51 | 2 | 46 |
| D | 42 | 2 | 58 |
| E | 63 | 2 | 52 |
| F | 58 | 2 | 50 |
| Commercial Product | 54 | 30 | 28 |

[a] on 100% cotton. Pretreatment - 35° C., 150 ppm water hardness, 3 clothes, 0.3 grams surface active agent per test: soiling - 5 drops of used motor oil: Final wash - 35° C., 150 ppm water hardness, 10 gram liquid detergent formulation.
[b] Conditions: 35° C., 150 ppm water hardness 2 test fabrics per test 0.3 grams surfactant per test
[c] 0.1% aqueous solution at 24.2° C.

The general surface activity of each of the compositions of this Example is apparent from the results reported. Although the soil removal activity of these particular compositions was uniformly poor in comparison with the commercial surfactant control, the comparable to or better soil release properties on cotton fabrics of these compositions is significant.

What is claimed is:

1. A nonionic composition that exhibits activity as a surface active agent which comprises the alkylene oxide—sulfur dioxide copolymer adducts of a water soluble alcohol having at least one oxyalkylene group in the chain which is represented by the general formula:

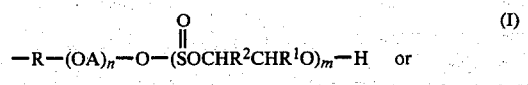

wherein R is an alkyl group, $R^{1,2,3,4}$, which can be the same or different, are hydrogen or an alkyl group having 1 or 2 carbon atoms, n is an integer of from 1 up to a value of about 1000, m is an integer of from 1 up to a value of about 1000, and OA is a divalent radical selected from the group consisting of oxyethylene units and mixtures of oxyethylene units and oxypropylene units having oxyporpylene units up to a ratio of about 1:1.

2. The nonionic composition of claim 1 wherein R is an alkyl group having from 1 to about 20 carbon atoms.

3. The nonionic composition of claim 1 wherein m is an integer having values from 3 to about 500.

4. The nonionic composition of claim 1 wherein n is an integer having values of 5 to about 500.